United States Patent
Arumugam et al.

(10) Patent No.: US 9,014,440 B2
(45) Date of Patent: Apr. 21, 2015

(54) DENTAL CYSTS DETECTOR

(75) Inventors: Banumathi Arumugam, Madurai (IN);
Raju Srinivasan, Madurai (IN);
Abhaikumar Varadhan, Madurai (IN)

(73) Assignee: Thiagarajar College of Engineering, Tamilnadu (IN)

( * ) Notice: Subject to any disclaimer, the term of this patent is extended or adjusted under 35 U.S.C. 154(b) by 1040 days.

(21) Appl. No.: 12/647,116

(22) Filed: Dec. 24, 2009

(65) Prior Publication Data
US 2011/0110574 A1 May 12, 2011

(30) Foreign Application Priority Data

Nov. 11, 2009 (IN) .......................... 2759/CHE/2009

(51) Int. Cl.
*G06K 9/00* (2006.01)
*A61B 6/14* (2006.01)
*G06T 7/00* (2006.01)
*A61B 6/00* (2006.01)

(52) U.S. Cl.
CPC .......... *A61B 6/14* (2013.01); *G06T 2207/30036* (2013.01); *G06T 2207/30096* (2013.01); *G06T 7/0044* (2013.01); *G06T 2207/10116* (2013.01); *G06T 7/0014* (2013.01); *A61B 6/5217* (2013.01)

(58) Field of Classification Search
USPC ...................................... 382/128–134; 378/62
See application file for complete search history.

(56) References Cited

U.S. PATENT DOCUMENTS

| 2003/0002723 A1* | 1/2003 | Li et al. ........................... 382/128 |
| 2005/0010106 A1* | 1/2005 | Lang et al. ..................... 600/425 |
| 2008/0002873 A1* | 1/2008 | Reeves et al. ................. 382/133 |

OTHER PUBLICATIONS

International Search Report and Written Opinion issued by the Australian Patent Office in PCT/IB2010/054344, dated Dec. 6, 2010.
Banumathi, et al., "Automated Diagnosis and Severity Measurement of Cyst in Dental X-ray Images using Neural Network", Biomedical Soft Computing and Human Sciences, vol. 14, No. 2, pp. 103-108, Apr. 2009.
Zacharaki et al., "An Automatic Registration-Fusion Scheme Based on Similarity Measures: An Application to Dental Imaging", 23rd Annual International Conference of the IEEE Engineering in Medicine and Biology Society, Oct. 25-28, 2001.
Han et al., "Radicular Cysts and Odontogenic Keratocysts Epithelia Classification Using Cascaded Haar Classifiers", Medical Imaging Understanding and Analysis, 2008, Proceedings of the 12th Annual Conference, Dundee, 2008 pp. 1-5.
(Continued)

*Primary Examiner* — Hoon Song
(74) *Attorney, Agent, or Firm* — Foley & Lardner LLP

(57) ABSTRACT

A system and method for detecting a cyst from a dental radiographic image is provided. The system and method comprises comparing the radiographic image to a plurality of template images, calculating a cross correlation coefficient between a plurality of regions in the radiographic image and a corresponding plurality of regions in the template image, determining a cyst region in the radiographic image based on a value of the cross correlation coefficient and computing a severity level of the cyst.

24 Claims, 4 Drawing Sheets

(56) References Cited

OTHER PUBLICATIONS

Yoshiura, K. et al., "Morphologic Analysis of Odontogenic Cysts with Computed Tomography", Oral and Maxillofacial Radiology, vol. 83, Issue 6, Jun. 1997, pp. 712-718.

Landini, G., "Quantitative Analysis of the Epithelial Lining Architecture in Radicular Cysts and Odontogenic Keratocysts", Head and Face Medicine, Feb. 17, 2006, pp. 1-9.

Gonzalez, R.C. et al., "Digital Image Processing," Second Edition, Pearson Education Incorporation, 2002.

Junior, O. F., et al., "Simple Bone Cyst versus Odontogenic Keratocyst: Differential Diagnosis by Digitized Panoramic Radiography," Dentomaxillofacial Radiology, The British Institute of Radiology, 2004, vol. 33, pp. 373-378.

Penedo, M.G., et al., "Computer-Aided Diagnosis: A Neural-Network-Based Approach to Lung Nodule Detection," IEEE Transactions on Medical Imaging, Dec. 1998, vol. 17, Issue 6, pp. 872-880.

Faber, T.D., et al., "Fourier Analysis Reveals Increased Trabecular Spacing in Sickle Cell Anemia," Journal of Dental Research, 2002, vol. 81, No. 3, pp. 214-218.

Venkatesan, P., et al., "Application of a Radial Basis Function Neural Network for Diagnosis of Diabetes Mellitus," Current Science, Nov. 10, 2006, vol. 91, No. 9, pp. 1195-1199.

\* cited by examiner

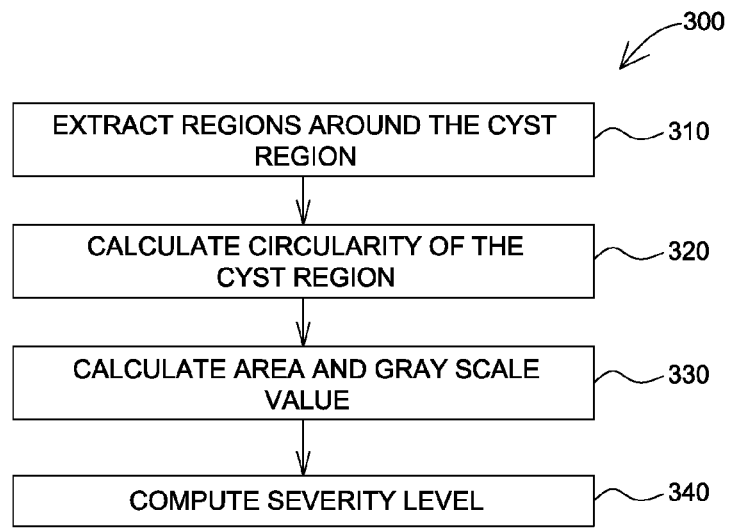

FIG. 3

| GRAY SCALE VALUE | AREA (PIXELS) | CIRCULARITY | SEVERITY |
|---|---|---|---|
| 0 - 40 | 1001 - 3000 | 0.75 - 1 | COMPLETELY PERFORATED. |
| 41 - 60 | 251 - 1000 | 0.61 - 0.75 | INVOLVES ONE CORTEX AND STARTED PERFORATING. |
| 61 - 150 | 200 - 250 | 0.5 - 0.6 | CONFINED WITH IN MEDULLARY BONE. (NOT ERODING BOTH CORTICAL). |

FIG. 4

| GRAY SCALE VALUE | LOW | | | MEDIUM | | | HIGH | | |
|---|---|---|---|---|---|---|---|---|---|
| AREA / CIRCULARITY | LOW | MEDIUM | HIGH | LOW | MEDIUM | HIGH | LOW | MEDIUM | HIGH |
| LOW | LOW | MEDIUM | MEDIUM | LOW | LOW | MEDIUM | HIGH | LOW | LOW |
| MEDIUM | MEDIUM | MEDIUM | HIGH | LOW | MEDIUM | HIGH | LOW | MEDIUM | MEDIUM |
| HIGH | MEDIUM | HIGH | HIGH | LOW | MEDIUM | HIGH | LOW | MEDIUM | MEDIUM |

FIG. 5

DENTAL CYSTS DETECTOR

CROSS REFERENCE TO RELATED APPLICATIONS

This application claims priority to Indian Patent Application Serial No. 2759/CHE/2009 filed Nov. 11, 2009, the contents of which are incorporated by reference herein in its entirety.

BACKGROUND

One of the most common dental pathologies is dental cysts. Cysts generally occur more often in the jaws than in any other bone. Usually they are round or oval in shape, resembling a fluid filled balloon. Cysts are normally radiolucent and grow slowly, and can sometimes causing displacement and resorption of the teeth. Clinically dental related cysts appear fluctuant inside the mouth.

Typically, detection of dental pathologies is performed by a dentist during a clinical examination of a patient. Sometimes extra oral swelling may be seen depending upon the nature and the extent of the cyst. By aspirating the fluid with a syringe inserted into the swelling, the dentist can roughly diagnose the cyst. However, the exact extension and number of teeth involved in the cystic region cannot be accurately determined.

In recent applications, dental diagnostic imaging methods are employed in confirming the presence and the extent of cysts, tumors, etc. in the oral cavity. Dental imaging techniques include magnetic resonance imaging (MRI), computed tomography (CT), ultrasound (US), and intra-oral and extra-oral radiography. It has been observed that dental radiographs greatly assist in the identification and evaluation of oral pathologies like dental cysts, tumor and cancer.

However, the image processing-based detection techniques currently employed are not automated, and diagnosis is generally performed by manually examining the radiographic image of the oral cavity. Therefore, detection using such techniques is usually subjective and may vary in accuracy due to factors such as viewing conditions and dentist expertise, among others. In addition, such techniques are not adequate to determine a severity level of the detected cysts.

SUMMARY

Briefly according to one embodiment of the present technique, a method for detecting an abnormality from a radiographic image is provided. The method comprises comparing data representative of the radiographic image to a plurality of template image data, calculating a cross correlation coefficient between a plurality of regions in the radiographic image data and a corresponding plurality of regions in the template image data, determining an abnormality region in the radiographic image data based on a value of the cross correlation coefficient, and computing a severity level of the abnormality.

In another embodiment, a method for dental cyst diagnosis is provided. The method comprises comparing data representative of a dental image to reference template image data, calculating a cross correlation coefficient for the image data and each template image data, determining a cyst region in the image data that comprises the cyst based on the cross correlation coefficient and computing a severity level of the cyst.

In another embodiment, a system for detecting a cyst from a radiographic image is provided. The system comprises memory circuit configured to store a plurality of template images. The system further includes image processing circuitry coupled to the memory circuit and configured to compare the radiographic image to a plurality of template images, to calculate a cross correlation coefficient between a plurality of regions in the radiographic image and a corresponding plurality of regions in the template image, to determine a cyst region in the radiographic image that comprises the cyst based on a value of the cross correlation coefficient, and to compute a severity level of the cyst.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 3 is a flow chart illustrating one technique by which a severity level of a cyst is determined;

FIG. 4 is a table depicting severity levels based on example values of circularity, area and gray scale values;

FIG. 5 is a table depicting severity levels for different values of the input parameters;

DETAILED DESCRIPTION

Figure 1:
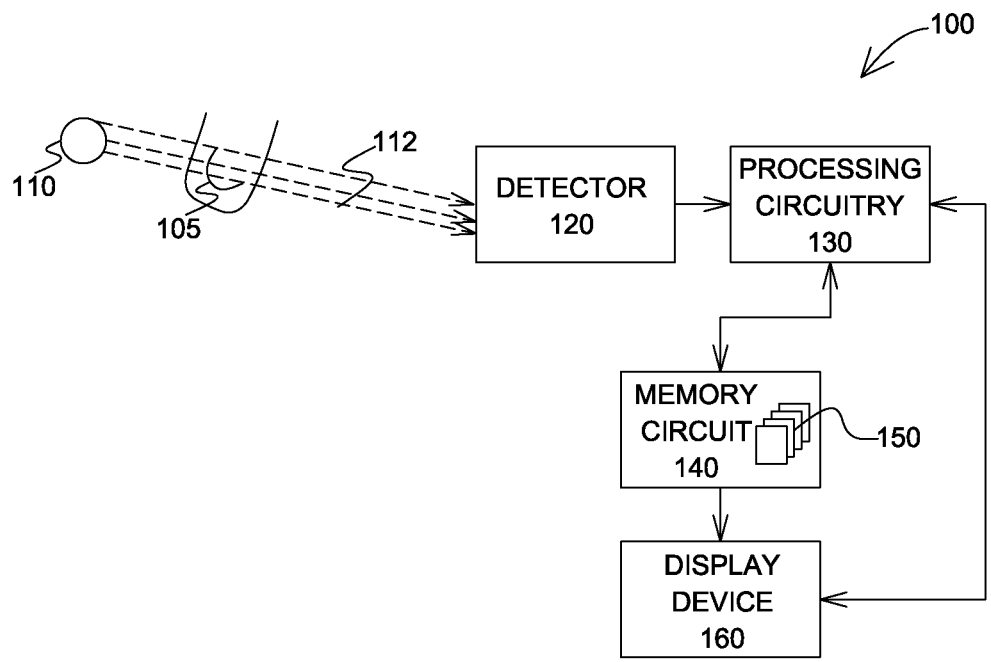
FIG. 1 is a diagrammatical representation of an example imaging system for detecting cysts from a dental radiographic images.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Example embodiments are generally directed to detection of dental cysts. The technique provides an automated diagnostic system that processes radiographic images of the oral cavity and detects dental cysts using image processing techniques, as will be described in detail below.

Referring now to FIG. 1, an example imaging system 100 for detecting cysts inside the mouth of a subject is illustrated. As used herein, the term "cyst" refers round or oval shaped closed sacs that occur more often in the jaws. As illustrated, the system 100 includes a radiation source 110, a detector 120, processing circuitry 130, memory circuit 140 and display device 160. Each block is described in further detail below.

Radiation source 110 is configured to transmit radiation 112 in the direction through an identified region of interest around the mouth 105. In one embodiment, the radiation source is an X-ray source. Detector 120 receives the radiation that passes through the region of interest and converts to corresponding lower energy photons, and subsequently to digital data.

Processing circuitry 130 is configured to suitably process the data collected from the detector 120 and generate an image of the region of interest. The image of the scanned region of interest is displayed on display device 160 or may be stored in memory circuit 140. Processing circuitry is configured to further analyze the image to detect a presence of cyst.

Memory circuit 140 is configured to store a plurality of template images 150. In one embodiment, the radiographic image generated by the processing circuitry 130 is also stored in memory circuit 140. As will be understood in those skilled in the art, although a single memory circuit is described here by way of example, the functions performed by the memory circuit may consist of more than one memory device associated with the system for storing radiographic images, template images and so forth.

The memory circuit 140 may include hard disk drives, optical drives, tape drives, random access memory (RAM), read-only memory (ROM), programmable read-only memory (PROM), redundant arrays of independent disks (RAID), flash memory, magneto-optical memory, holographic memory, bubble memory, magnetic drum, memory stick, Mylar® tape, smartdisk, thin film memory, zip drive, and so forth.

As discussed above, the processing circuitry is configured to process and analyze the radiographic image to detect cysts. The manner in which a cyst is detected from a radiographic image is described in further detail below with reference to FIG. 2.

Figure 2:
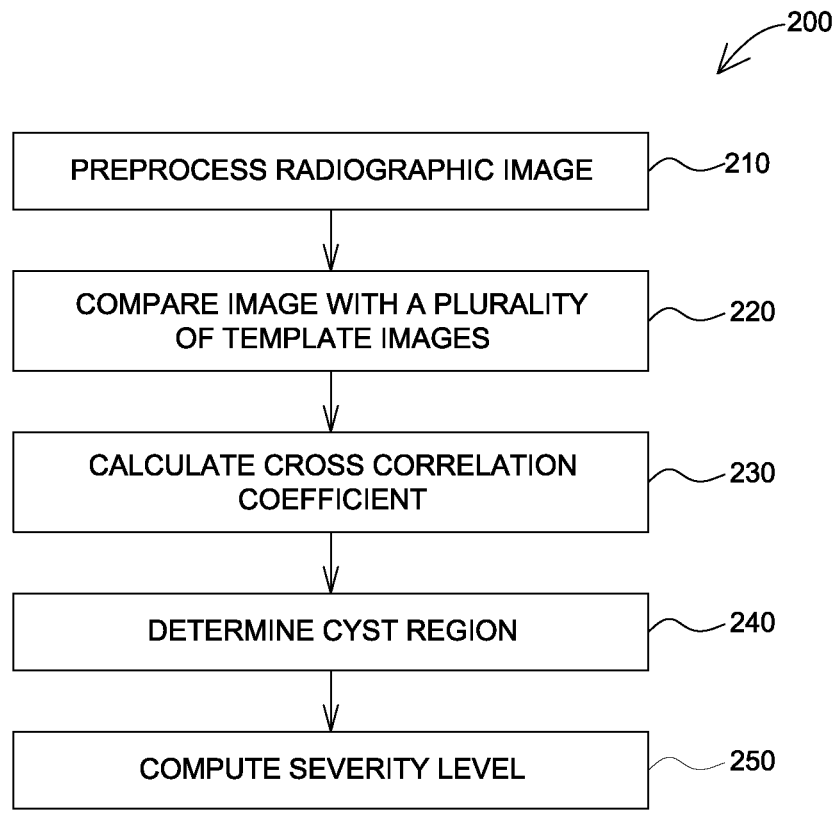
FIG. 2 is a flow chart illustrating one technique by which a cyst is determined from a dental radiographic image.

FIG. 2 is a flow chart depicting one method to detect cysts from a dental radiographic image. In one embodiment, the steps of the process 200 described below are performed by processing circuitry of the imaging system as shown in FIG. 1. Each step is described in further detail below. At step 210, the radiographic image is preprocessed. In one embodiment, a contrast stretching algorithm is applied on the image to enhance the edges of various structures within the image. Structures within the image may include teeth, jaw bone, cysts, etc.

At step 220, the radiographic image is compared to a plurality of template images. As used herein, a template image is a reference image of a typical dental cyst. In one embodiment, the radiographic image is compared to at least five template images. It should be appreciated that, while reference is made in the present discussion to "images", in the actual processing, image data (i.e., data representing features of the teeth, jaw bone, cysts, etc.) is used in processing, comparisons, diagnosis, and so forth. For simplicity, however, such data is referred to as the image itself, although the image data may or may not be used to produce an actual image. Similarly, while reference is made to a "template" image, this "image" may consist of data that is combined for a reference set, such as to arrive at values that are indicative of features sought or detectable in the image under consideration.

At step 230, a cross correlation coefficient is calculated between a plurality of regions in the radiographic image and a corresponding plurality of regions in the template image. In one embodiment, each plurality of regions includes one pixel. In one embodiment, the cross correlation coefficient $\gamma(s, t)$ is normalized and is computed using the following equation:

$$\gamma(s, t) = \frac{\sum_x \sum_y [f(x, y) - \overline{f}(x, y)][w(x-s, y-t) - \overline{w}]}{\left\{ \sum_x \sum_y \left[ \frac{f(x, y) -}{\overline{f}(x, y)} \right]^2 \sum_x \sum_y [w(x-s, y-t) - \overline{w}]^2 \right\}^{\frac{1}{2}}} \quad \text{Equation (1)}$$

where s=0, 1, 2, . . . , M−1, t=0, 1, 2, . . . , N−1, $\overline{w}$ is the average value of the pixel in w(x,y), $\overline{f}(x, y)$ is the average value of f(x, y) in the region coincident with the current location of w, and the summations are taken over the coordinates common to both w and f.

At step 240, a cyst region is identified (if present) in the radiographic image based on a value of the cross correlation coefficient. In one embodiment, a high value of the cross correlation coefficient indicates a presence of a cyst. In one embodiment the normalized cross correlation coefficients determined using equation (1) are converted to corresponding gray scale values and are referred to generally as expanded normalized cross correlation coefficients (ENCC). In a specific embodiment, the ENCC values vary from 0 to 255.

In one embodiment, artificial neural networks with radial basis functions are used to categorize regions in the radiographic image based on the ENCC values. In one embodiment, the regions are categorized as highly suspicious, suspicious, slightly suspicious and not suspicious. At step 250, a severity level of the cyst is computed. The manner in which the severity level of the cyst is computed is described in further detail below.

FIG. 3 is a flow chart depicting one method to determine a severity level of a cyst detected in a dental radiographic image. As described in the flow chart of FIG. 2, a cyst region is identified in the dental radiographic image based on a value of the cross correlation coefficients. The severity level of the cyst is determined as described in the following steps of process 300. At step 310, regions surrounding the identified cyst regions are extracted. In one embodiment, the regions are extracted using the connectivity property. At step 320, a circularity of the cyst region is calculated. In one embodiment, the circularity is calculated by comparing an area of a region inside an equivalent circle with the area of the cyst region. At step 330, a gray scale value and an area of the cyst region is calculated based on the circularity of the cyst region. In one embodiment, the gray scale value and the area is calculated when the calculated circularity exceed a threshold value. At step 340, a severity level is computed for the cyst region based on the circularity, the area and the gray scale value.

FIG. 4 is a table illustrating severity levels for corresponding values of circularity, area and gray scale values. For example, for a circularity ranging from 0.75-1, area of the cyst region between 1001-3000 pixels and a gray scale value that ranges from 0-40, the cyst is completely perforated. Similarly for a circularity ranging of 0.61-0.75 of the cyst region between 251 and 1000 pixels and a gray scale value that ranges from 41-60, indicates that the cyst involves one cortex and has begun perforating. For a circularity ranging of 0.5-0.6 of the cyst region between 200 and 251 pixels and a gray scale value that ranges from 61-150, indicates that the cyst is confined within the medullary bone.

In one embodiment, fuzzy logic technique is used to compute the severity level as shown in FIG. 5. FIG. 5 is a table showing severity levels computed based on input parameters using a fuzzy logic technique. Each input parameter namely circularity of the cyst region, the area and the gray scale values is marked by a high, medium or low level. Similarly, the output of the fuzzy logic technique which is indicative of the severity level of the cyst is also given a high, medium or low rating based on the combination of the input parameters. In one embodiment, a low severity level indicates that the cyst region is confined within the medullary bone. A medium severity level indicates that the cyst has begun perforating and a high severity level indicates a completely perforated.

Figure 6:
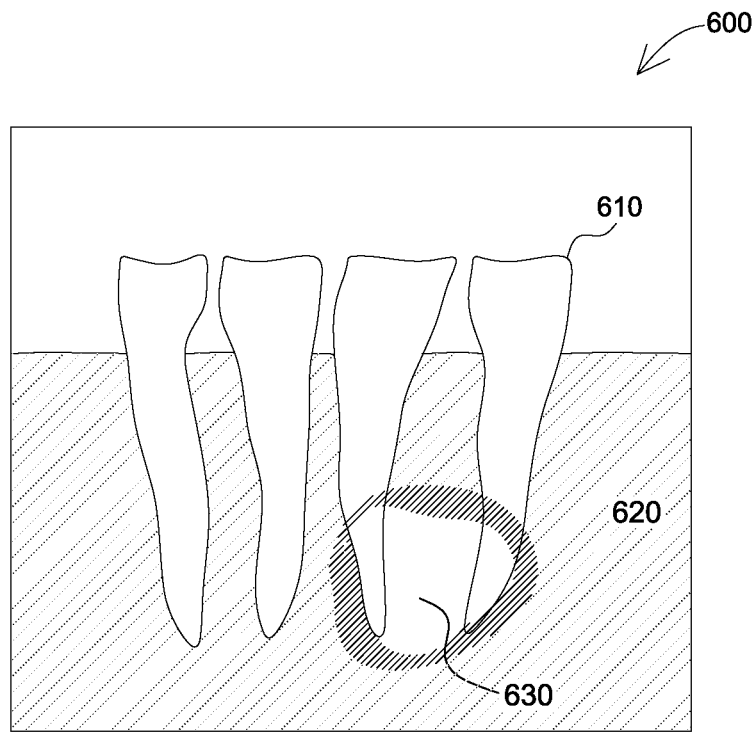
FIG. 6 is an example of a dental radiographic image.

The techniques described above assist in the accurate detection of dental cysts from a dental radiographic image. FIG. 6 is an example dental radiograph image 600 comprising a plurality of features such as teeth 610, tissue 620 and potential cyst region 630. Upon application of the techniques described herein accurate detection and severity level of dental cysts are determined from the dental radiographic image.

Figure 7:
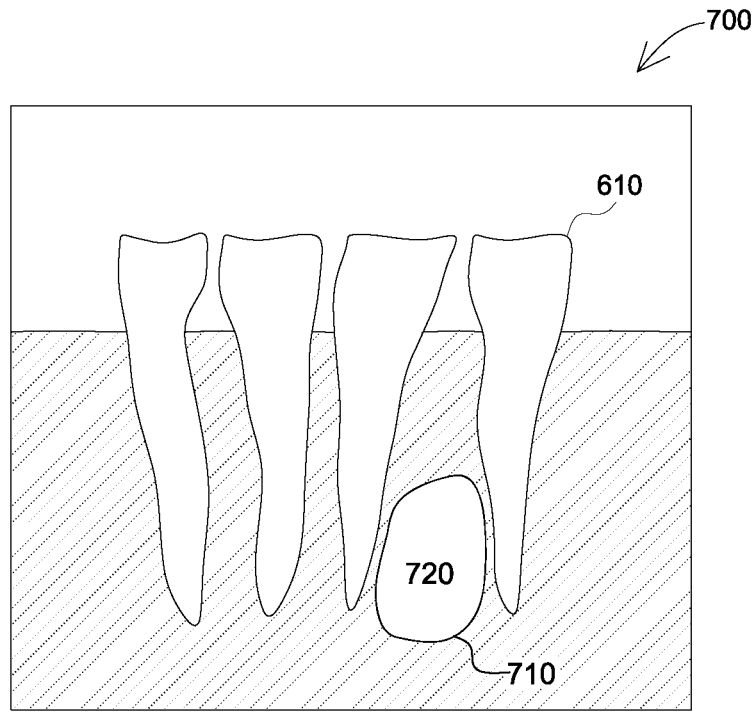
FIG. 7 is an example of a processed dental radiographic image that depicts the dental cyst.

FIG. 7 is an example of a processed dental radiographic image 700 in which a boundary 710 of the cyst region 720 has been clearly identified. Based on the area of the identified cyst region, a gray scale value of the cyst region and a circularity of the cyst region, a severity level of the cyst is computed as described in the flow chart of FIG. 3.

In an embodiment applying the above described techniques provide accurate detection of a cyst from the dental radiographic image. In addition, by employing fuzzy logic techniques, a severity level of the cyst is also determined by comparing parameters such as the area of the cyst region, a gray scale value and the circularity of the cyst region. The technique assists dentists to accurately diagnose and determine a corresponding treatment plan.

Figure 8:
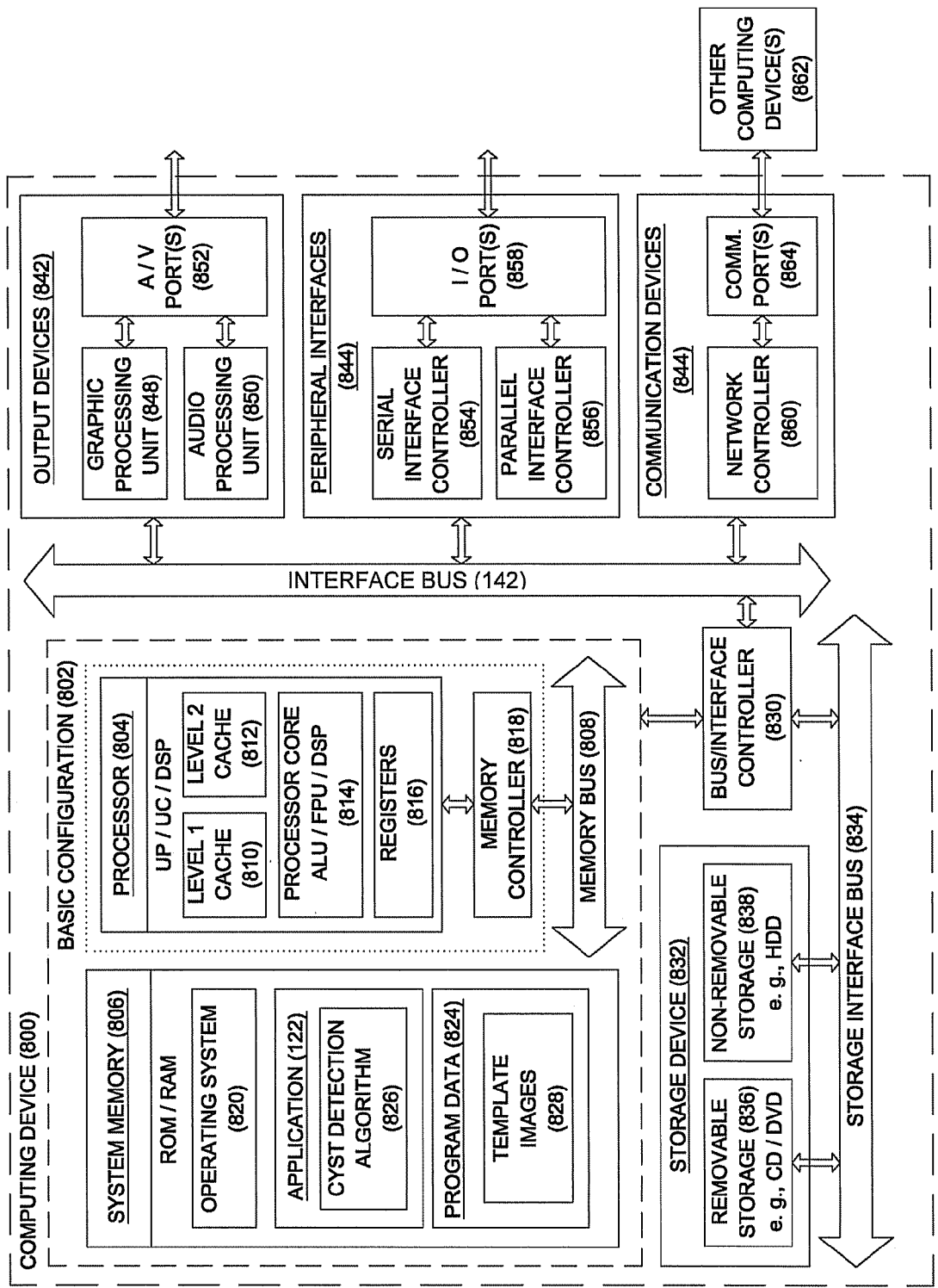
FIG. 8 is a block diagram of an embodiment of a computing device that may be used to implement the present techniques.

FIG. 8 is a block diagram illustrating an example computing device 800 that is arranged for detecting cysts from a dental radiographic image in accordance with the present disclosure. In a very basic configuration 802, computing device 800 typically includes one or more processors 804 and a system memory 806. A memory bus 808 may be used for communicating between processor 804 and system memory 806.

Depending on the desired configuration, processor 804 may be of any type including but not limited to a microprocessor (µP), a microcontroller (µC), a digital signal processor (DSP), or any combination thereof. Processor 804 may include one more levels of caching, such as a level one cache 810 and a level two cache 812, a processor core 814, and registers 816. An example processor core 814 may include an arithmetic logic unit (ALU), a floating point unit (FPU), a digital signal processing core (DSP Core), or any combination thereof. An example memory controller 818 may also be used with processor 804, or in some implementations memory controller 818 may be an internal part of processor 804.

Depending on the desired configuration, system memory 806 may be of any type including but not limited to volatile memory (such as RAM), non-volatile memory (such as ROM, flash memory, etc.) or any combination thereof. System memory 806 may include an operating system 820, one or more applications 822, and program data 824. Application 822 may include a cyst detection algorithm 826 that is arranged to the functions as described herein including those described with respect to process 200 of FIG. 2 and process 300 of FIG. 3. Program Data 824 may include template images 828 that may be useful for comparing with the radiographic image as will be further described below. In some embodiments, application 822 may be arranged to operate with program data 824 on operating system 820 such that cyst are detected from dental radiographic images as described herein. This described basic configuration 802 is illustrated in FIG. 8 by those components within the inner dashed line.

Computing device 800 may have additional features or functionality, and additional interfaces to facilitate communications between basic configuration 802 and any required devices and interfaces. For example, a bus/interface controller 830 may be used to facilitate communications between basic configuration 802 and one or more data storage devices 832 via a storage interface bus 834. Data storage devices 832 may be removable storage devices 836, non-removable storage devices 838, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 806, removable storage devices 836 and non-removable storage devices 838 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 800. Any such computer storage media may be part of computing device 800.

Computing device 800 may also include an interface bus 840 for facilitating communication from various interface devices (e.g., output devices 842, peripheral interfaces 844, and communication devices 846) to basic configuration 802 via bus/interface controller 830. Example output devices 842 include a graphics processing unit 848 and an audio processing unit 850, which may be configured to communicate to various external devices such as a display or speakers via one or more A/V ports 852. Example peripheral interfaces 844 include a serial interface controller 854 or a parallel interface controller 856, which may be configured to communicate with external devices such as input devices (e.g., keyboard, mouse, pen, voice input device, touch input device, etc.) or other peripheral devices (e.g., printer, scanner, etc.) via one or more I/O ports 858. An example communication device 846 includes a network controller 860, which may be arranged to facilitate communications with one or more other computing devices 862 over a network communication link via one or more communication ports 864.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 800 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 800 may also be implemented as a personal computer including both laptop computer and non-laptop computer configurations.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method for detecting an abnormality from a radiographic image, the method comprising:
   comparing, at a processing system, data representative of the radiographic image to reference template image data;
   calculating, at the processing system, a cross correlation coefficient between a plurality of regions in the data representative of the radiographic image and a corresponding plurality of regions in the reference template image data;
   determining, at the processing system, an abnormality region in the data representative of the radiographic image based on a value of the cross correlation coefficient; and
   computing, at the processing system, a severity level of the abnormality region.

2. The method of claim 1, wherein the determining the abnormality region comprises using an artificial neural network with a radial basis function.

3. The method of claim 1, wherein the severity level is computed based on at least one of an area of the abnormality region, a gray scale value of the abnormality region, and a circularity of the abnormality region.

4. The method of claim 1, further comprising preprocessing the data representative of the radiographic image prior to comparing the data representative of the radiographic image with the reference template image data.

5. The method of claim 1, wherein the radiographic image comprises a dental image, and wherein the abnormality region comprises a cyst.

6. The method of claim 1, wherein the reference template image data is derived from at least five template images.

7. The method of claim 1, further comprising normalizing the cross correlation coefficient for each region in the data representative of the radiographic image and converting the cross correlation coefficient to a gray scale value.

8. The method of claim 1, wherein each region of the plurality of regions in the data representative of the radiographic image comprises one pixel.

9. The method of claim 1, wherein the abnormality region is the region in the data representative of the radiographic image with a highest value of the cross correlation coefficient.

10. A method for dental cyst diagnosis, the method comprising:
    comparing, at a processing system, data representative of a dental image to reference template image data;
    calculating, at the processing system, a cross correlation coefficient between the data representative of the dental image and the reference template image data;
    determining, at the processing system, a cyst region in the data representative of the dental image that comprises a cyst based on the cross correlation coefficient; and
    computing, at the processing system, severity level of the cyst.

11. The method of claim 10, wherein the determining the cyst region comprises using an artificial neural network with a radial basis function.

12. The method of claim 10, wherein the severity level is computed based on at least one of an area of the cyst region, a gray scale value of the cyst region, and a circularity of the cyst region.

13. The method of claim 10, further comprising preprocessing the data representative of the dental image using contrast stretching prior to comparing the data representative of the dental image to the reference template image data.

14. A system for detecting a cyst from a radiographic image, the system comprising:
    a memory circuit; and
    template image processing circuitry coupled to the memory circuit and configured to:
      compare data representative of the radiographic image to reference template image data;
      calculate a cross correlation coefficient between a plurality of regions in the data representative of the radiographic image and a corresponding plurality of regions in the reference template image data;
      determine a cyst region in the data representative of the radiographic image that comprises the cyst based on a value of the cross correlation coefficient, and
      compute a severity level of the cyst.

15. The system of claim 14, wherein the template image processing circuitry is configured to detect the cyst region using an artificial neural network with a radial basis function.

16. The system of claim 14, wherein the severity level is computed based on at least one of an area of the cyst region, a gray scale value of the cyst regio and a circularity of the cyst region.

17. The system of claim 14, wherein the template image processing circuitry is configured to preprocess the data representative of the radiographic image prior to comparing the data representative of the radiographic image with the reference template image data.

18. The system of claim 14, wherein the template image processing circuitry is configured to compare data representative of the radiographic image to reference template image data derived from at least five template images.

19. The system of claim 14, wherein the template image processing circuitry is configured to normalize the cross correlation coefficient for each region in the data representative of the radiographic image and convert the cross correlation coefficient to a gray scale value.

20. The system of claim 14, wherein the cyst region corresponds to a region in the data representative of the radiographic image with a highest value of the cross correlation coefficient.

21. The method of claim 1, wherein the computing a severity level of the abnormality region comprises assigning a relative severity value corresponding to the severity level of the abnormality region, and wherein the relative severity value is indicative of a condition of an abnormality depicted in the abnormality region.

22. The method of claim 1, wherein the severity level is computed based on an area of the abnormality region, a gray scale value of the abnormality region, and a circularity of the abnormality region.

23. The method of claim 1, wherein the computing a severity level of the abnormality region is performed after a determination of the existence of the abnormality region.

24. The method of claim 1, wherein the computing a severity level of the abnormality region is separate from a determination of the existence of the abnormality region.

* * * * *

UNITED STATES PATENT AND TRADEMARK OFFICE
CERTIFICATE OF CORRECTION

| | | |
|---|---|---|
| PATENT NO. | : 9,014,440 B2 | Page 1 of 1 |
| APPLICATION NO. | : 12/647116 | |
| DATED | : April 21, 2015 | |
| INVENTOR(S) | : Arumugam et al. | |

It is certified that error appears in the above-identified patent and that said Letters Patent is hereby corrected as shown below:

In the Drawings

In Fig. 8, Sheet 4 of 4, delete "COMMUNICATION DEVICES (844)" and insert -- COMMUNICATION DEVICES (846) --, therefor.

In Fig. 8, Sheet 4 of 4, delete "INTERFACE BUS(142)" and insert -- INTERFACE BUS(840) --, therefor.

In Fig. 8, Sheet 4 of 4, delete "UP/UC/DSP" and insert -- µP/µC/DSP --, therefor.

In Fig. 8, Sheet 4 of 4, delete "APPLICATION(122)" and insert -- APPLICATION(822) --, therefor.

In the Specification

In Column 4, Line 48, delete "200 and 251" and insert -- 200 and 250 --, therefor.

In the Claims

In Column 9, Line 18, in Claim 10, delete "system, severity" and insert -- system, a severity --, therefor.

In Column 9, Line 43, in Claim 14, delete "coefficient," and insert -- coefficient; --, therefor.

In Column 10, Line 6, in Claim 16, delete "cyst regio and" and insert -- cyst region, and --, therefor.

Signed and Sealed this
Fifteenth Day of September, 2015

Michelle K. Lee
*Director of the United States Patent and Trademark Office*